US00PP16116P3

(12) United States Plant Patent
Smaal

(10) Patent No.: US PP16,116 P3
(45) Date of Patent: Nov. 15, 2005

(54) *KALANCHOE* PLANT NAMED 'PELLINORE'

(50) Latin Name: *Kalanchoe blossfeldiana*
Varietal Denomination: Pellinore

(75) Inventor: Andres Smaal, Aalsmeer (NL)

(73) Assignee: A.B. Breeding BV, Kwakel (NL)

( * ) Notice: Subject to any disclaimer, the term of this patent is extended or adjusted under 35 U.S.C. 154(b) by 96 days.

(21) Appl. No.: 10/928,062

(22) Filed: Aug. 27, 2004

(65) Prior Publication Data

US 2005/0081271 P1 Apr. 14, 2005

Related U.S. Application Data

(63) Continuation-in-part of application No. 10/644,669, filed on Aug. 20, 2003, now abandoned, which is a continuation of application No. 09/993,456, filed on Nov. 19, 2001, now abandoned.

(51) Int. Cl.[7] ..... A01H 5/00

(52) U.S. Cl. ..... Plt./339

(58) Field of Search ..... Plt./339

(56) References Cited

PUBLICATIONS

Netherlands PBR Certificate KLN271 (Denomination Accepted on Aug. 5, 1998)—in Dutch.

UPOV–ROM GTITM Computer Database, 2003/05, GTI Jouve Retrieval Software, citation for 'Pellinore'.

European Union Community Plant Variety Office Decision No. R121 relating to 'Pellinore' dated Sep. 11, 2000.

*Primary Examiner*—Bruce R. Campell
*Assistant Examiner*—S. B. McCormick-Ewoldt
(74) *Attorney, Agent, or Firm*—Wood, Phillips, Katz, Clark & Mortimer

(57) ABSTRACT

A new and distinct cultivar of *Kalanchoe* plant named 'Pellinore' is provided. This new cultivar is characterized by its bright pink flowers, dark green foliage, compact growth habit and excellent basal branching.

1 Drawing Sheet

Figure 1:
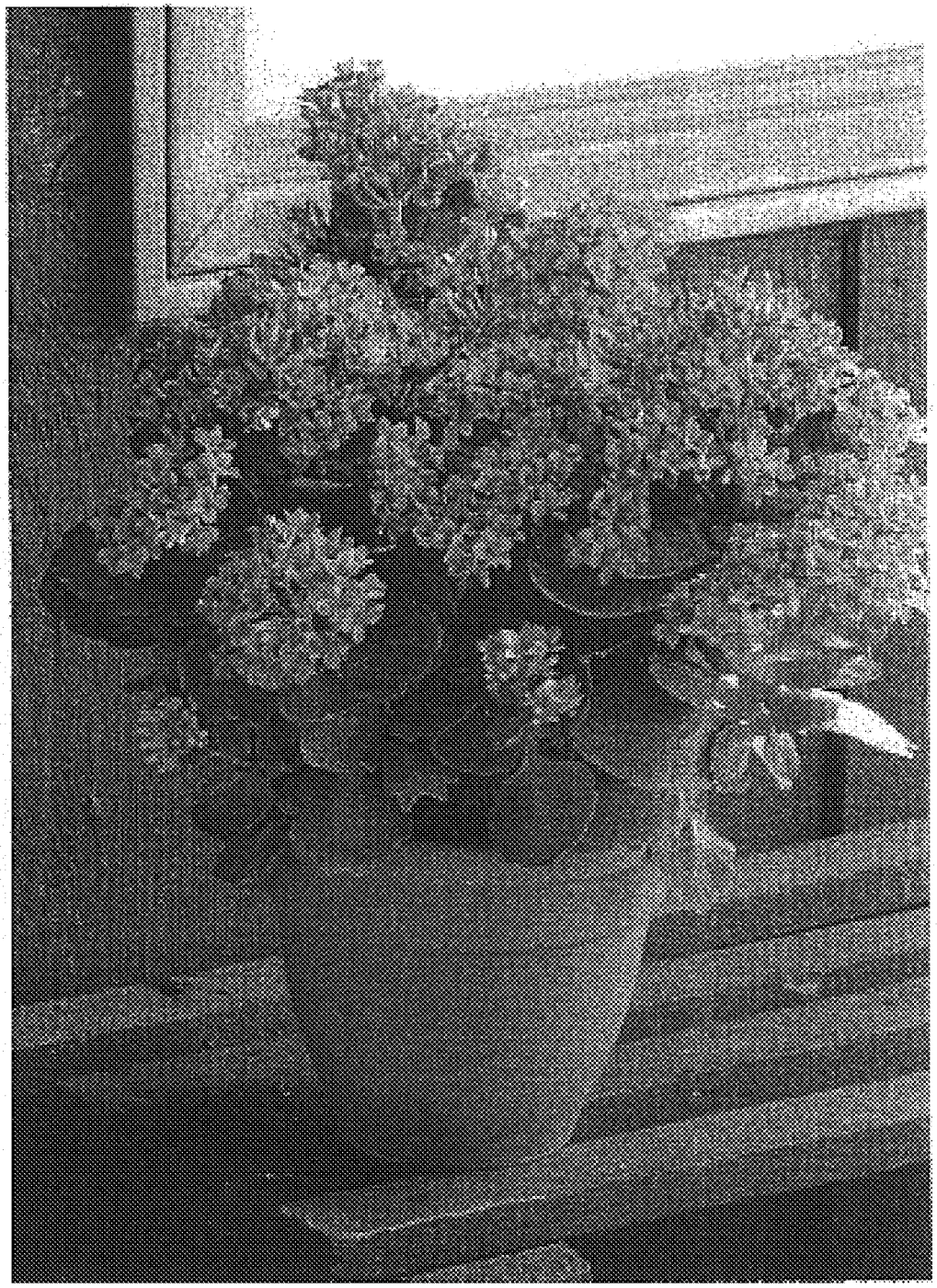

Latin name of genus and species of plant claimed: *Kalanchoe blossfeldiana.*
Variety denomination: 'Pellinore'.

BACKGROUND OF THE INVENTION

The present invention comprises a new and distinct *Kalanchoe* plant, botanically known as *Kalanchoe blossfeldiana*, and hereinafter referred to by the cultivar name 'Pellinore'.

The new cultivar was developed by the inventor through a controlled breeding program during August 1996 in the Netherlands. The male (pollen) parent of 'Pellinore' was the proprietary *Kalanchoe blossfeldiana* selection designated #92111-7 (not patented). The female (seed) parent of 'Pellinore' was the proprietary *Kalanchoe blossfeldiana* selection designated #93074 (not patented) characterized by its light pink flowers. 'Pellinore' was discovered and selected as a flowering plant within the progeny of the stated cross by the inventor in June 1997.

Asexual reproduction of the new cultivar by terminal cuttings has demonstrated that the characteristics of the new cultivar as herein described are firmly fixed and retained through successive generations of such asexual propagation.

SUMMARY OF THE INVENTION

It was found that the cultivar of the present invention:

(a) exhibits bright pink flowers, (b) forms dark green foliage, (c) exhibits a good basal branching character, and (d) exhibits a compact upright growth habit.

The new cultivar of the present invention can be compared to 'Light Jacqueline' (U.S. Plant Pat. No. 10,268). In side by comparisons with 'Light Jacqueline', it is found that the new cultivar is more compact, less floriferous and exhibits flowers of a brighter pink color. A detailed comparison can be found in Table 1.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown in a greenhouse at West Chicago, Ill., U.S.A.

DETAILED BOTANICAL DESCRIPTION

The 'Pellinore' cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Jan. 4, 2001 between 9:00 and 9:30 a.m. under natural daylight. The plants used for the following observations and measurements were produced from cuttings taken from stock plants and grown in West Chicago, Ill. in 10 cm pots for sixteen (16) weeks. Plants were grown in a double poly carbonate covered greenhouse under conditions comparable to those used in commercial practice while utilizing a soilless growth medium and maintaining temperatures of approximately 82° F. during the day and approximately 66° F. during the night. Plants were exposed to three weeks of long days followed by 9 weeks of short days. Growth regulators were applied as follows: B nine, 3000 ppm at days 17 and 28 and 1500 ppm at day 42.

Classification:

*Botanical.*—*Kalanchoe blossfeldiana*, cultivar 'Pellinore'.

Parentage:

*Male (pollen) parent.*—Proprietary *Kalanchoe blossfeldiana* selection #92111-7.

*Female (seed) parent.*—Proprietary *Kalanchoe blossfeldiana* selection #93074.

Propagation:

*Type cutting.*—Terminal tip.

*Time to initiate roots.*—Approximately 7–14 days with the shorter times generally being experienced in the summer and the longer times in the winter.

*Time to develop roots.*—Approximately 21 days.

*Root description.*—Fibrous, branching.

Plant description:

*Habit of growth.*—Moderately vigorous with good basal branching. A mature plant, at 16 weeks after the planting of an unrooted cutting, commonly measures approximately 13.9 cm in height and approximately 16.1 cm in width.

*Branching habit.*—Typically forms one main stem 10 cm in length and 5 mm in diameter and 8 to 12 lateral branches approximately 8.3 cm in length and 4 mm in diameter. Internode length on main stem: Approximately 1.3 cm.

*Plant form.*—Upright and mounded.

*Foliage.*—Form: Simple. Arrangement: Opposite. Shape: Ovate with obtuse apex, rounded base and crenate margin. Texture: Glabrous, succulent. Size of mature foliage: Approximately 7.8 cm in length and approximately 6.2 cm in width. Color of mature foliage: Upper surface between 137A and 139A; lower surface closest to 137B. Petiole length: Approximately 1 cm. Petiole diameter: Approximately 7 mm. Petiole color: 144B.

Flower description:

*Flower habit.*—Freely flowering.

*Natural flowering season.*—Early January. Flowering time is dependent on temperature, light intensity and other growing conditions.

*Flowering response time.*—Approximately 11 weeks.

*Inflorescence type.*—Dichasial cymes.

*Flowers borne.*—Above foliage.

*Flower longevity.*—Approximately 7 days.

*Fragrance.*—None.

*Quantity of flowers.*—Approximately 36 flowers on main stem and 23 flowers on each lateral branch.

*Flower buds.*—Shape: Elliptical, becoming elongated as it matures. Size just before opening: Length is approximately 7 mm, width is approximately 4 mm. Color is 32C.

*Flower.*—Salverform. Corolla: Diameter is approximately 1.5 cm, depth is approximately 6 mm and aspect is cupped. Corolla tube is approximately 9 mm long, 3 mm in diameter.

*Mature flower color.*—Upper surface of petal is closest to 43C at opening, becoming 55B with midib bush of 54B at maturity and fading to 55D with midrib blush of 55B at senescence; lower surface of petals is closest to 55 D.

*Petals.*—Number: Four. Shape: Obovate with cuspidate apex, rounded base and entire margin. Approximate size: 8 mm in length, 6 mm in width. Aspect: Slightly concave. Texture: Glabrous. Appearance: Somewhat iridescent.

*Sepals.*—Number: Four. Shape: Lanceolate with acuminate apex, entire margin. Size: 7 mm in length, 1 mm in width. Texture: Smooth. Color: Upper and lower surface: 144B.

*Peduncle.*—Approximately 2 cm in length and 4 mm in diameter.

*Pedicle length.*—Approximately 5 mm.

*Reproduction organs.*—Androecium: 8 stamens arranged in two groups of four — one group being shorter than the other. Anther shape is oblong and flat; length is approximately 0.5 mm. Pollen color is 3B. Gynoeciuim: Stigma shape is flat. Appearance is crystalline, colorless and transparent. Style length is approximately 1 mm; color is 154B. Ovary: 4 celled, 7 mm in length. Ovary color: 144B.

Seed development: Seed development has not been observed.

Disease resistance: Resistance to known *Kalanchoe* pathogens has not been observed.

TABLE 1

| CHARACTERISTIC | 'PELLINORE' | 'LIGHT JACQUELLINE' |
|---|---|---|
| PLANT HEIGHT | 13.9 cm | 21.8 cm |
| NUMBER OF BRANCHES | About 10 | 12 |
| COROLLA DIAMETER | 1.5 cm | 1.4 cm |
| PETAL COLOR-FULLY OPENED - UPPER SURFACE - MATURE FLOWER | 55B with midrib blush of 54B | Between 68A and 68B |
| APPROXIMATELY NUMBER OF FLOWERS PER PANT | 266 | 355 |
| LEAF LENGTH | about 7.8 cm | 13.7 cm |
| LEAF WIDTH | 6.2 cm | 5.9 cm |

What is claimed is:

1. A new and distinct cultivar of *Kalanchoe* plant named 'Pellinore' substantially as herein shown and described which:

(a) exhibits bright pink flowers, (b) forms dark green foliage, (c) exhibits a good basal branching character, and (d) exhibits a compact upright growth habit.

* * * * *